(12) United States Patent  
Harton et al.

(10) Patent No.: US 9,138,532 B2
(45) Date of Patent: Sep. 22, 2015

(54) GANGABLE INJECTION PORT HOLDER

(71) Applicants: Christopher E. Harton, Allen, TX (US); Jeff Richard Summers, McKinney, TX (US)

(72) Inventors: Christopher E. Harton, Allen, TX (US); Jeff Richard Summers, McKinney, TX (US)

(73) Assignee: Quest Medical, Inc., Allen, TX (US)

( * ) Notice: Subject to any disclaimer, the term of this patent is extended or adjusted under 35 U.S.C. 154(b) by 0 days.

(21) Appl. No.: 13/930,763

(22) Filed: Jun. 28, 2013

(65) Prior Publication Data

US 2014/0034169 A1  Feb. 6, 2014

Related U.S. Application Data

(60) Provisional application No. 61/665,338, filed on Jun. 28, 2012.

(51) Int. Cl.
| | |
|---|---|
| A61M 5/14 | (2006.01) |
| A61M 5/168 | (2006.01) |
| A61M 39/02 | (2006.01) |
| A61M 39/24 | (2006.01) |
| A61M 39/00 | (2006.01) |
| A61M 39/10 | (2006.01) |

(52) U.S. Cl.
CPC ......... *A61M 5/1418* (2013.01); *A61M 5/16827* (2013.01); *A61M 39/00* (2013.01); *A61M 39/02* (2013.01); *A61M 2039/1072* (2013.01); *A61M 2039/1077* (2013.01); *A61M 2039/1083* (2013.01); *A61M 2039/246* (2013.01); *A61M 2039/2433* (2013.01); *Y10T 137/9029* (2015.04)

(58) Field of Classification Search
CPC .............. A61M 5/1408; A61M 39/02; A61M 5/16827; A61M 2039/2433
USPC ............. 604/81, 83, 246, 247, 256, 533, 537, 604/539, 905; 137/798, 859; D24/108, 112, D24/121, 127, 128, 129
See application file for complete search history.

(56) References Cited

U.S. PATENT DOCUMENTS

| | | | | |
|---|---|---|---|---|
| 5,020,562 | A | * | 6/1991 | Richmond et al. ......... 137/15.01 |
| 5,360,413 | A | * | 11/1994 | Leason et al. .................. 604/249 |
| 6,083,205 | A | * | 7/2000 | Bourne et al. ................. 604/246 |
| 6,364,861 | B1 | * | 4/2002 | Feith et al. .................... 604/247 |
| 6,508,791 | B1 | * | 1/2003 | Guerrero ........................ 604/183 |
| 8,496,624 | B2 | * | 7/2013 | Baxter et al. .............. 604/164.11 |
| 2004/0250864 | A1 | * | 12/2004 | Zelson .......................... 137/859 |
| 2012/0209243 | A1 | * | 8/2012 | Yan ............................... 604/500 |

* cited by examiner

*Primary Examiner* — Theodore Stigell
*Assistant Examiner* — Amber Stiles
(74) *Attorney, Agent, or Firm* — GrayRobinson, P.A.

(57) ABSTRACT

A gangable injection port holder including a series of receptacles for receiving swabable access valves that are themselves serially ganged together by tubing or complementary Luer slip connections. The receptacles are integrally formed onto a base with a side wall to allow the swabable access valves during use to be oriented vertically resting on the base or horizontally resting on the side wall. The base may be segmented, with each segment containing at least one of the receptacles. The segments may be easily snapped together in order to quickly assemble the desired number of receptacles intended to be used during a surgical procedure.

20 Claims, 21 Drawing Sheets

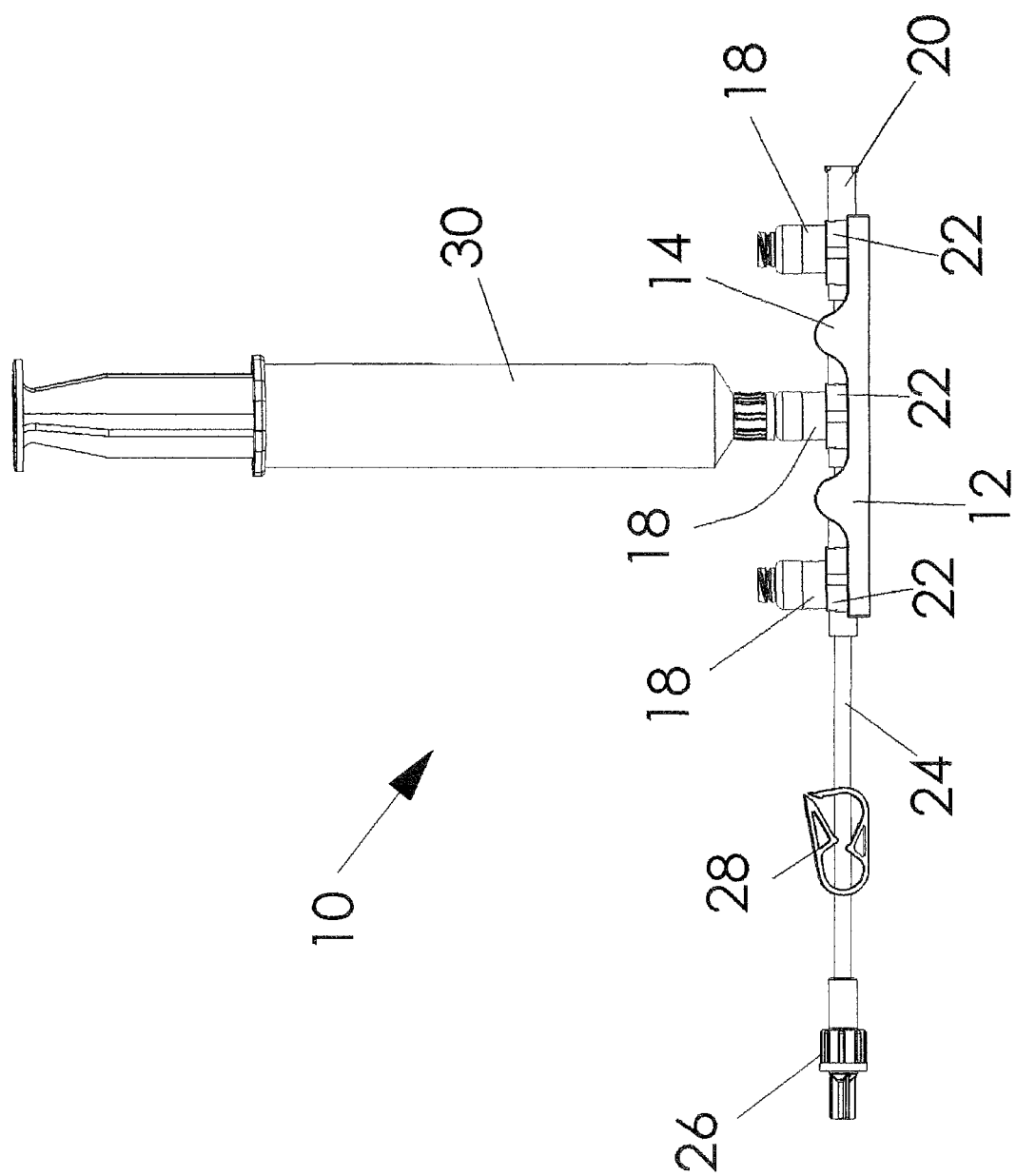

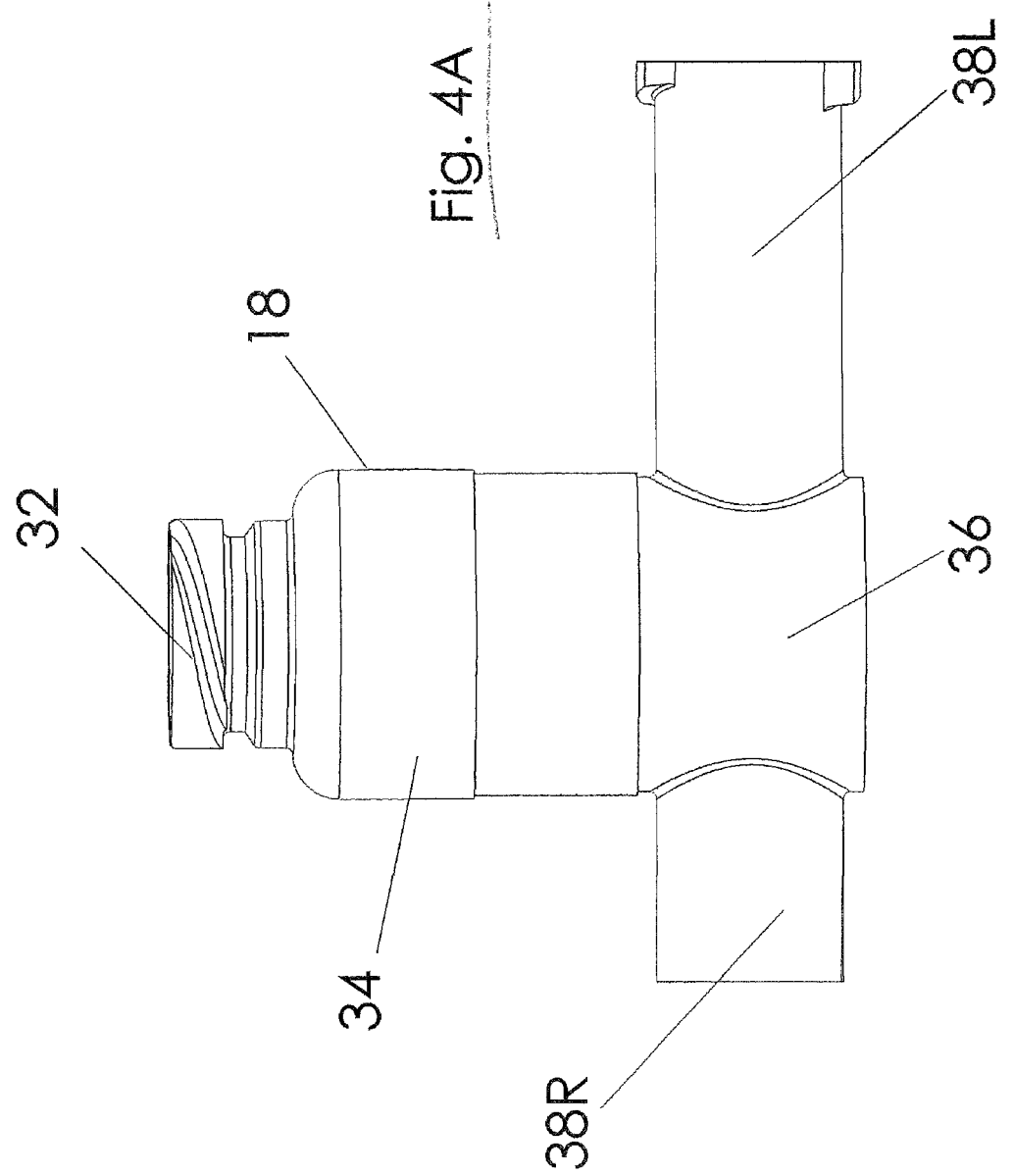

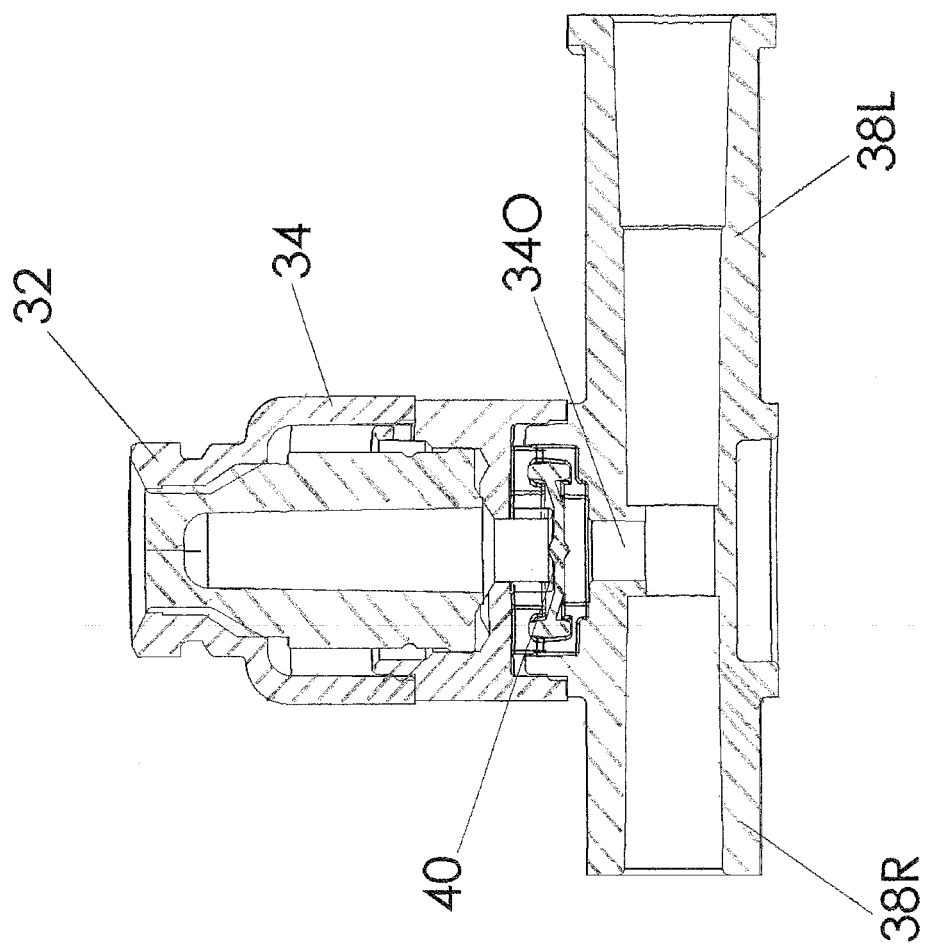

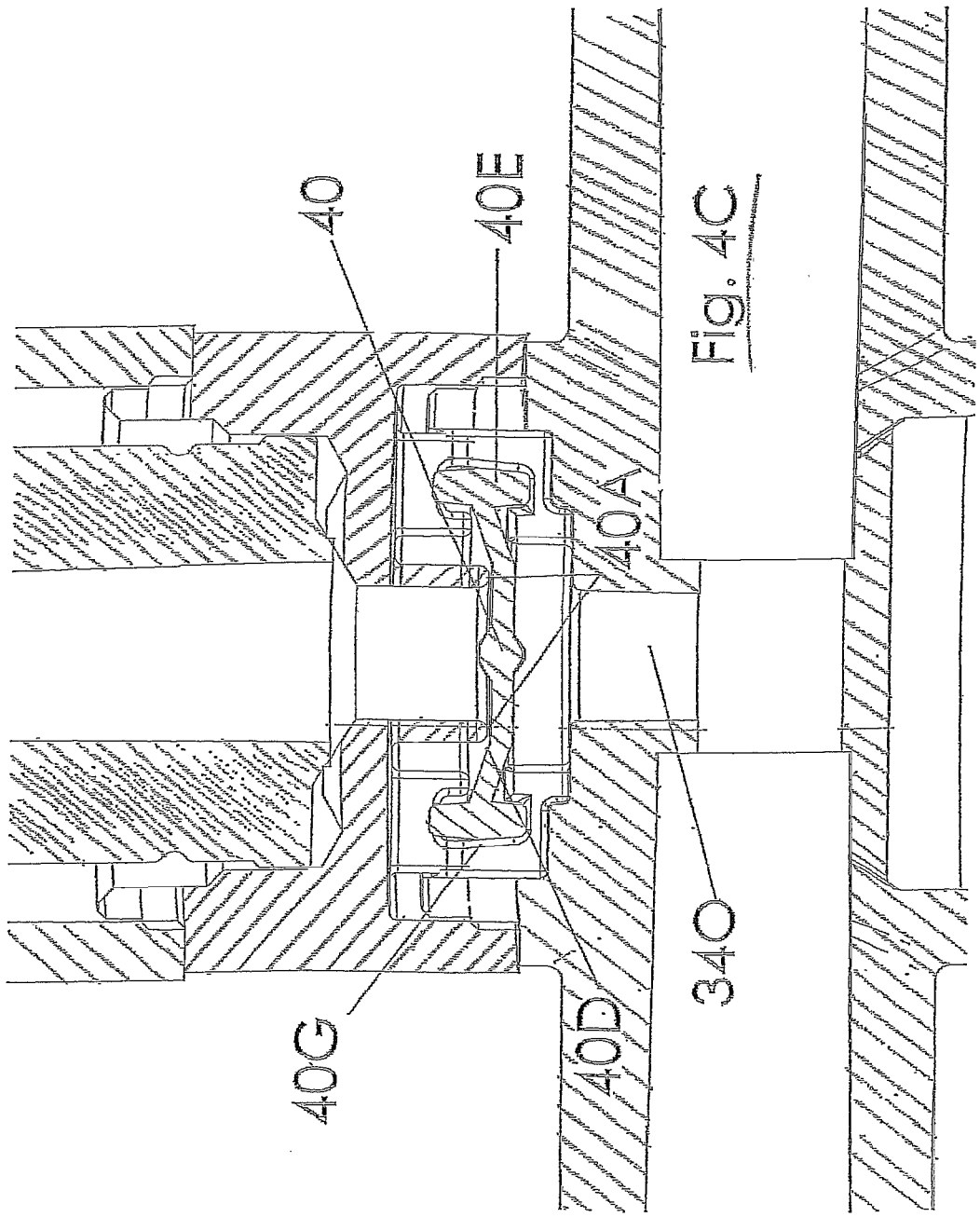

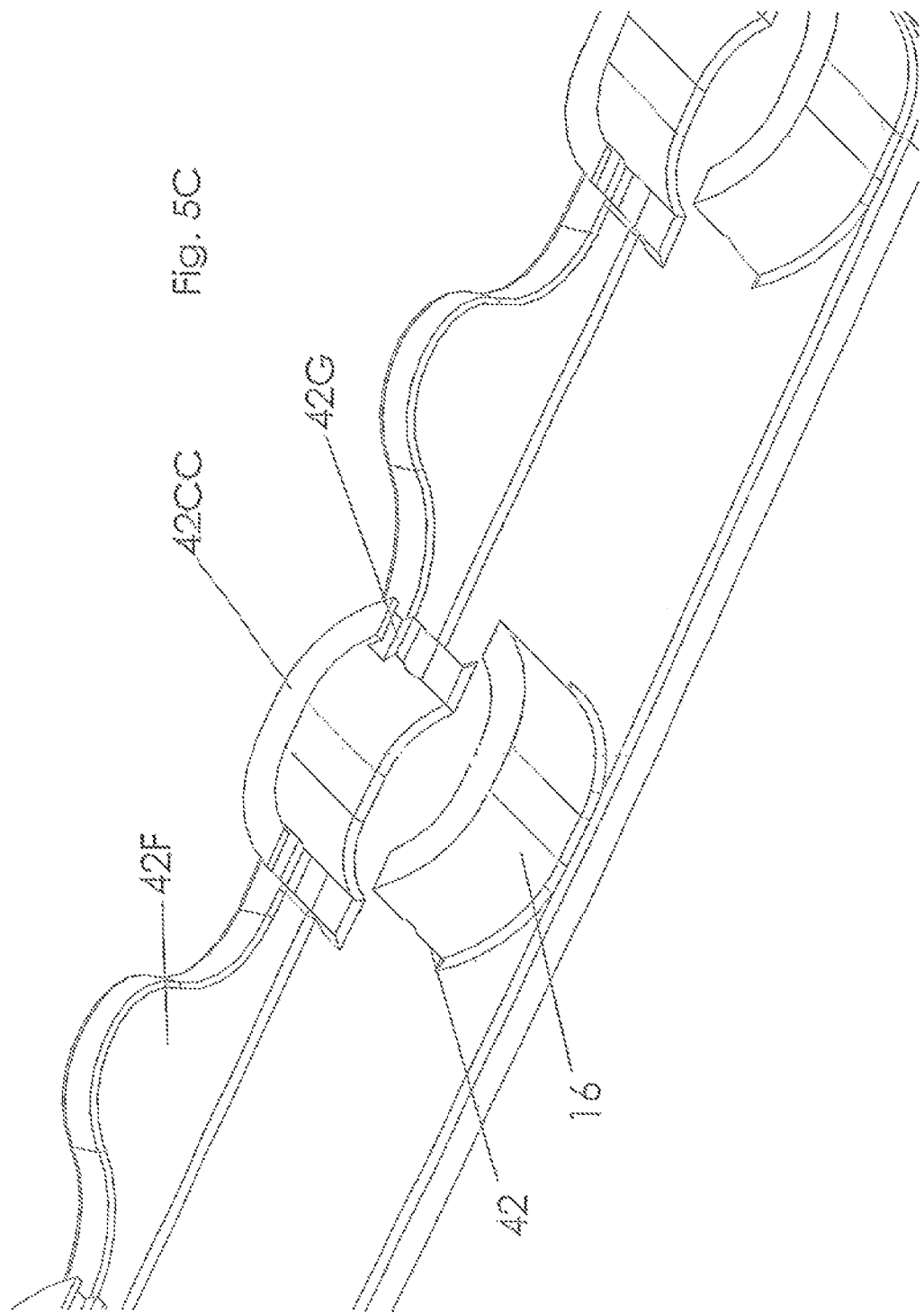

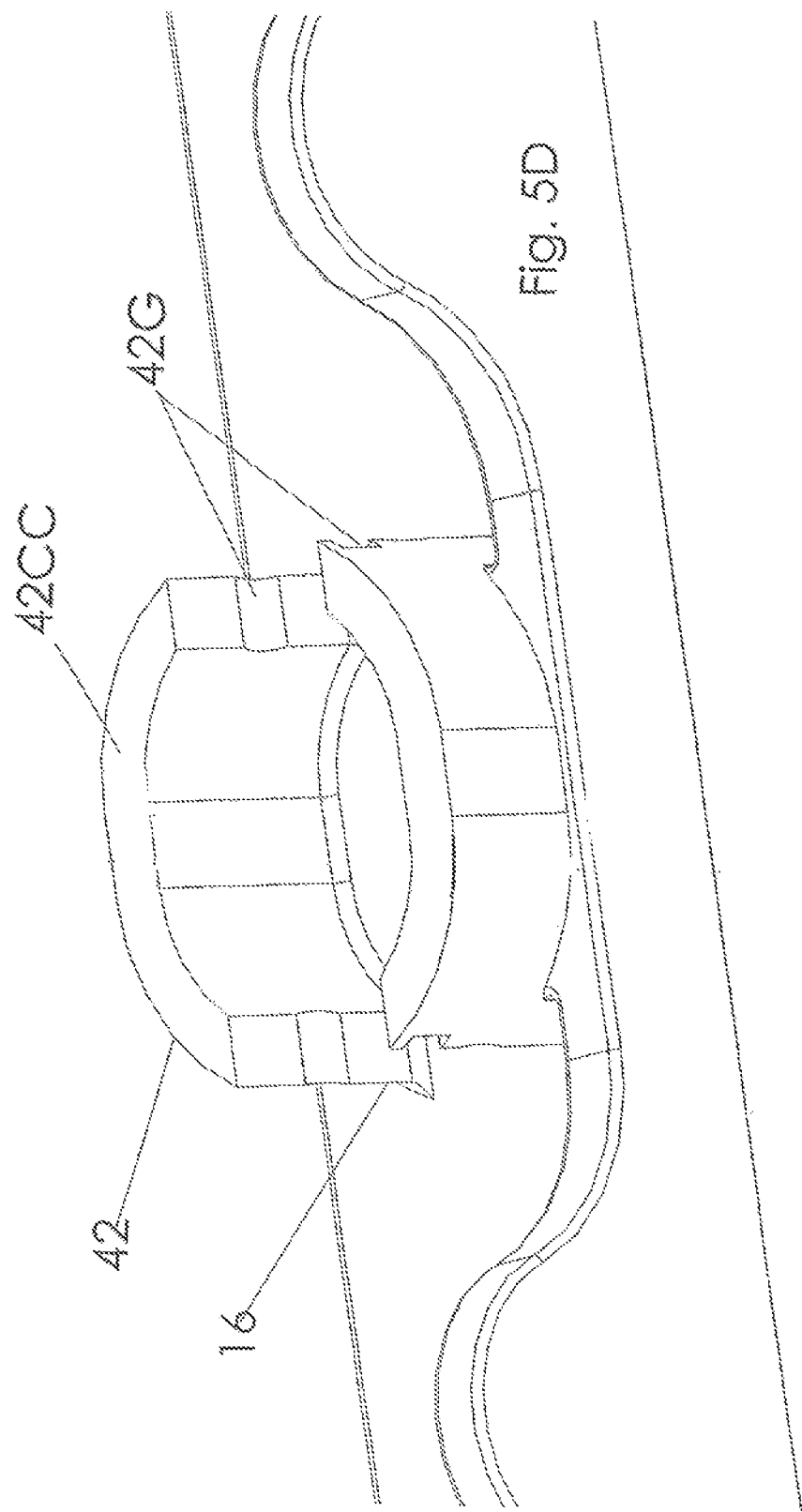

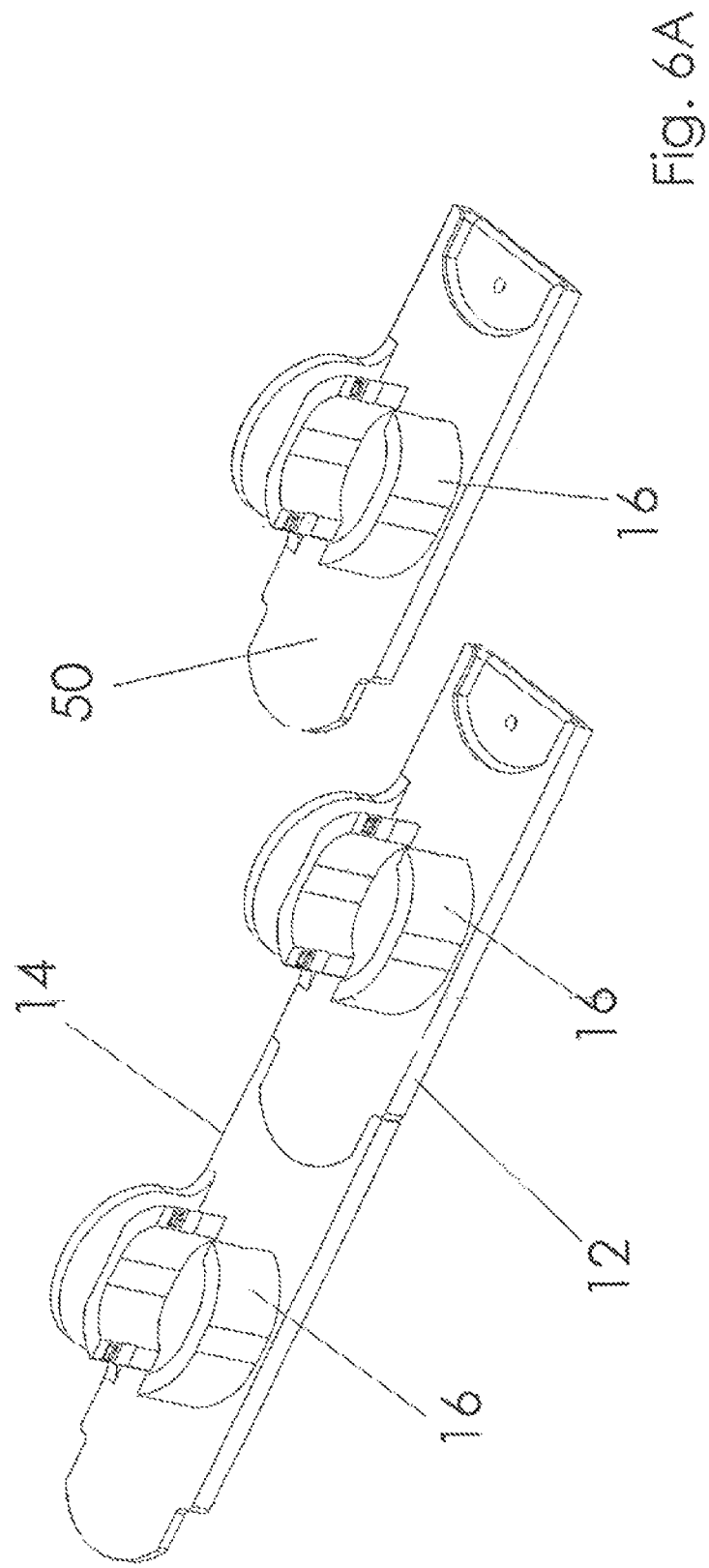

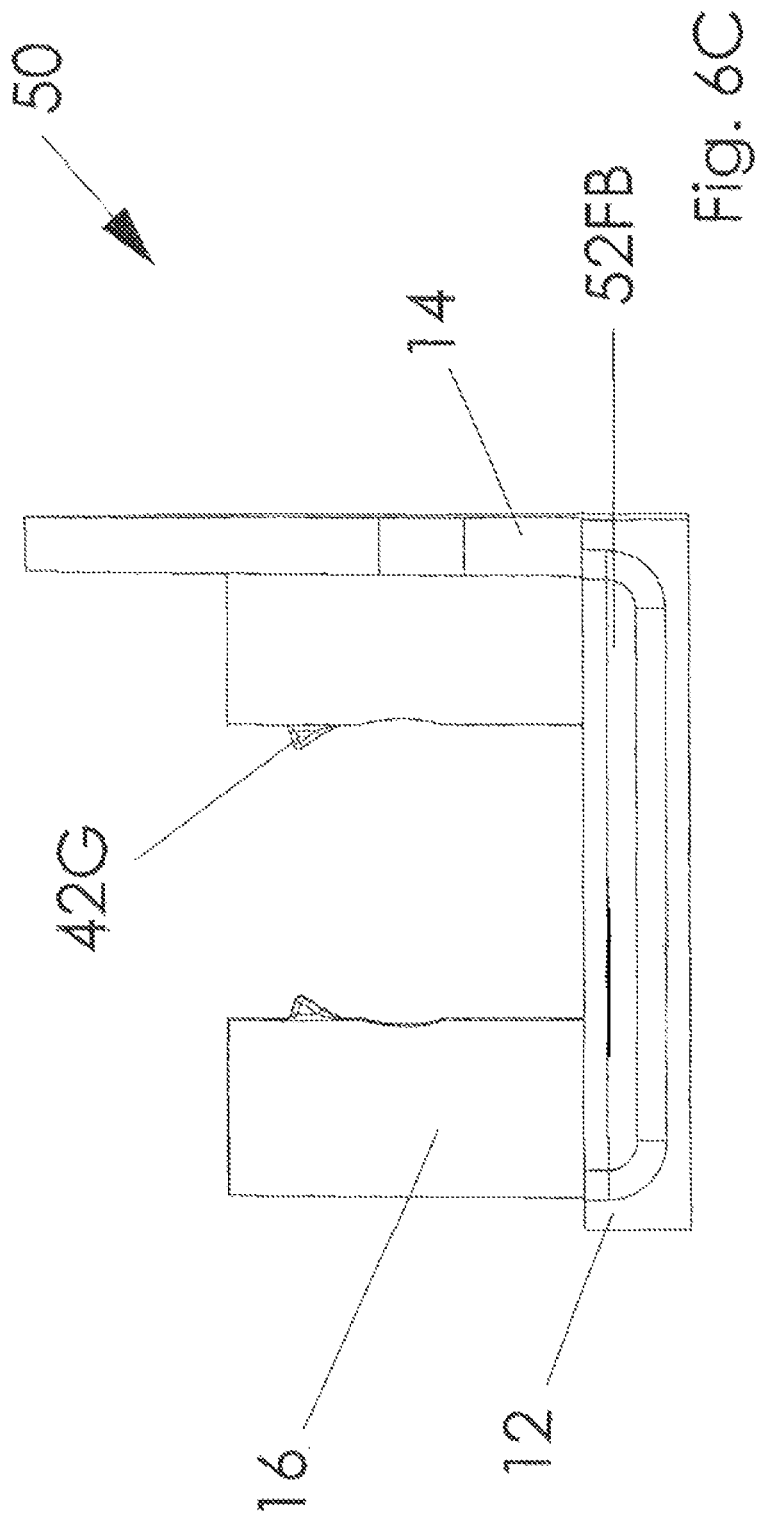

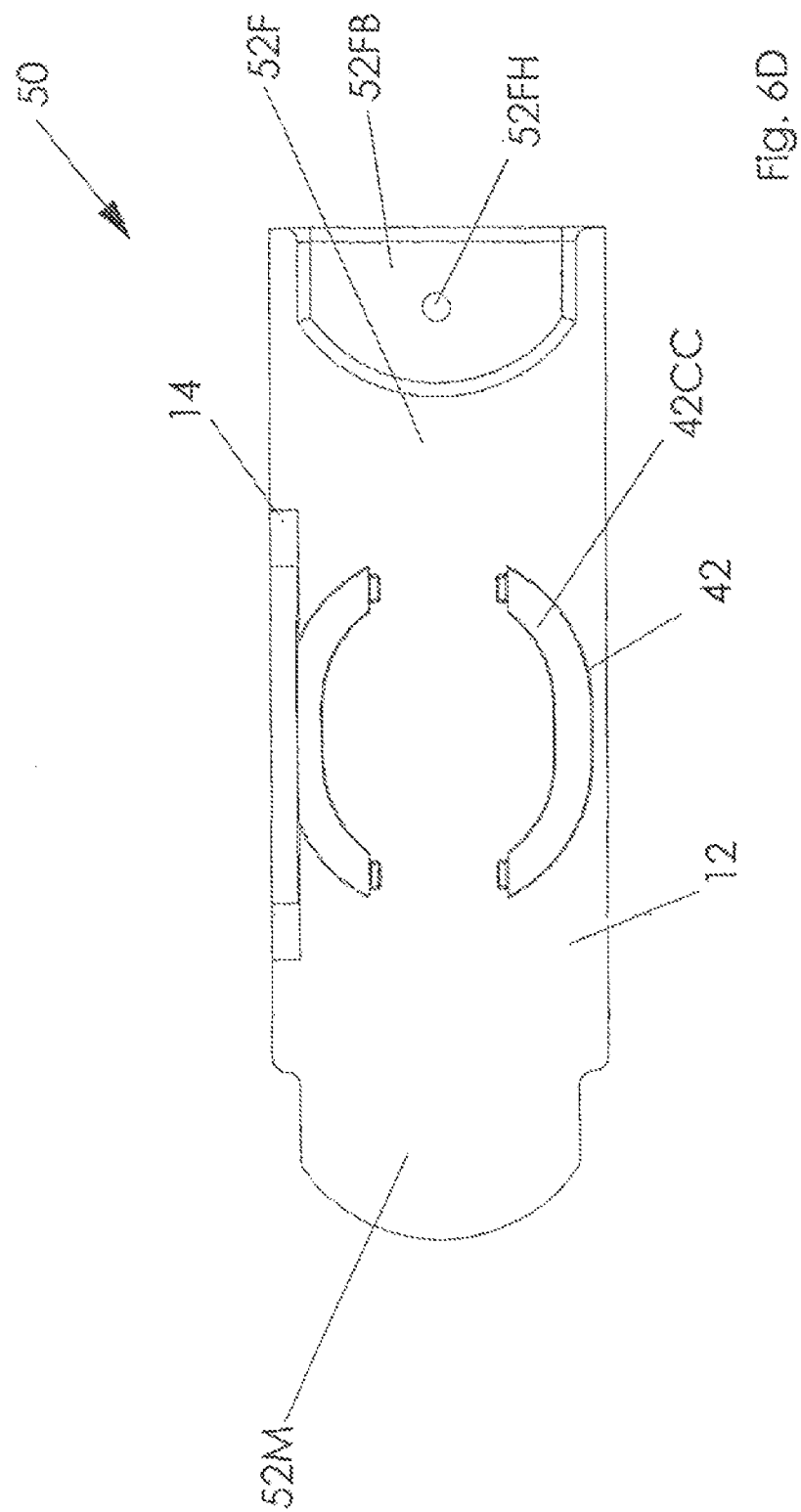

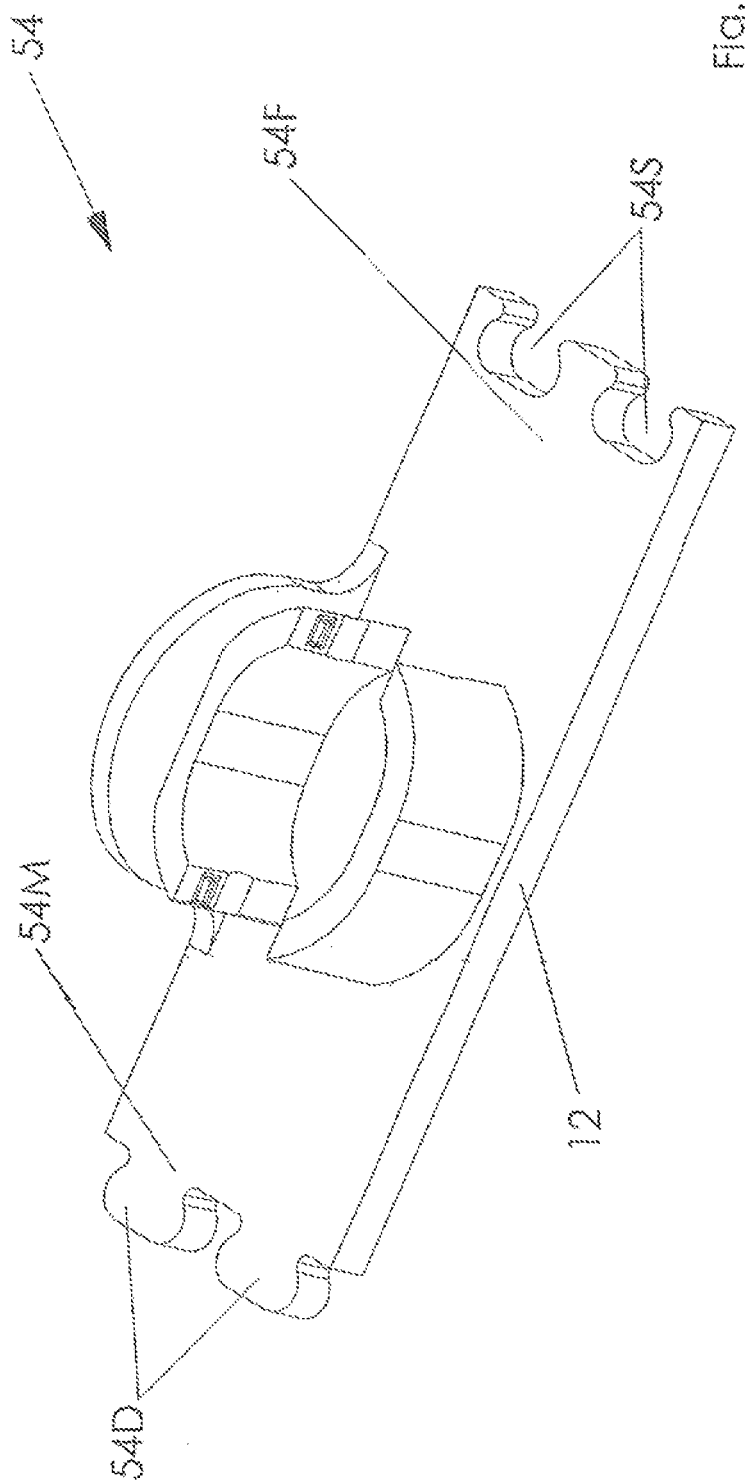

GANGABLE INJECTION PORT HOLDER

CROSS-REFERENCE TO RELATED APPLICATIONS

This application claims the benefit of provisional application No. 61/665,338, filed Jun. 28, 2012, the disclosure of which is incorporated by reference herein.

BACKGROUND OF THE INVENTION

1. Field of the Invention

This invention relates to manifolds for intravenous (IV) systems. More particularly, this invention relates to IV manifolds that are particularly suited for use in administering anesthesia medications.

2. Description of the Background Art

Presently there exist many components to intravenous (IV) systems designed to deliver medications to a patient or to draw blood from the patient. Historically, IV systems employed a variety of ports that allowed a medical practitioner to access the port via a hypodermic needle to administer fluids to the patient or to withdraw blood from the patient. In more recent years, such ports have been supplanted by needleless access ports containing a swabable valve with a Luer fitting that allowed the medical practitioner to directly connect the syringe to the needleless access port without the use of a hypodermic needle. Needleless access ports are universally preferred over ports that are accessed by means of a hypodermic needle to eliminate the risk of inadvertent needle pricks to the medical practitioner that could otherwise result in the spreading of a disease, particularly AIDS.

In the cardiac field, it is often necessary to administer a number of different medicines to the patient. Hence, IV systems have been developed which employ a series of needleless access valves that are "ganged" closely together. Ganged needleless access valves allow the use of a plurality of syringes of medications to be connected in fluid communication with an IV line throughout the surgical procedure for the selective administration of the medicine as needed. Representative ganged needleless access valves by Quest Medical, Inc. are sold under the trademarks "Q2®" "Checkmate®", "Q2 Multiport" and "Q2 T-Extension Set." Quest's ganged needleless access valves eliminate the use of numerous needleless access valves, minimize residual volume or "dead space" in the injection ports, allow easy one-handed operation and allow syringes to remain attached for selective injection throughout a surgical procedure. Quest's ganged swabable access ports further include integrated check valves to prevent retrograde flow from the patient into the respective syringes. Quest's ganged swabable access ports may be conveniently mounted on IV pole holders for easy, stable delivery of the medicine.

Quest's ganged access ports have employed specialized housings for containing the needleless access valves in a variety of combinations of two-port to six-port gang arrangements. Consequently, the prior art ganged access ports are expensive to manufacture and must be stocked in a variety of arrangements.

Therefore, it is an object of this invention to provide an improvement which overcomes the aforementioned inadequacies of the prior art devices and provides an improvement which is a significant contribution to the advancement of the ganged access port art.

Another object of this invention is to provide a ganged injection port which utilizes swabable access valves that are ganged together at T-sites by tubing and then mounted in base in close proximity to one another.

Another object of this invention is to provide a ganged access injection port for conventional swabable valves which are manufactured in interlocking segments to allow quick assembly of the number of segments desired for a particular surgical procedure.

The foregoing has outlined some of the pertinent objects of the invention. These objects should be construed to be merely illustrative of some of the more prominent features and applications of the intended invention. Many other beneficial results can be attained by applying the disclosed invention in a different manner or modifying the invention within the scope of the disclosure. Accordingly, other objects and a fuller understanding of the invention may be had by referring to the summary of the invention and the detailed description of the preferred embodiment in addition to the scope of the invention defined by the claims taken in conjunction with the accompanying drawings.

SUMMARY OF THE INVENTION

For the purpose of summarizing this invention, this invention comprises a gangable injection port holder that includes a series of receptacles for receiving swabable access valves that are themselves serially ganged together by tubing or complementary Luer slip connections. The receptacles integrally formed onto a base with a side wall to allow the swabable access valves during use to be oriented vertically resting on the base or horizontally resting on the side wall. The present invention also includes segmentation of the base and side wall, with each segment containing one of the receptacles. The segments may be easily snapped together in order to quickly assemble the desired number of receptacles intended to be used during a surgical procedure. For example, when a four-port assembly is desired, four segments are snapped together to create a four-receptacle ganged assembly. When six are desired, six segments are snapped together, and so on.

The foregoing has outlined rather broadly the more pertinent and important features of the present invention in order that the detailed description of the invention that follows may be better understood so that the present contribution to the art can be more fully appreciated. Additional features of the invention will be described hereinafter which form the subject of the claims of the invention. It should be appreciated by those skilled in the art that the conception and the specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a fuller understanding of the nature and objects of the invention, reference should be had to the following detailed description taken in connection with the accompanying drawings in which:

FIGS. 1B and 1C respectively showing typical uses of the holder laying horizontally on a table or positioned upright on the table;

FIG. 4A is a side elevational view of one of the swabable access valves, FIG. 4B is a cross-sectional view thereof and FIG. 4C is an enlarged cross-sectional view thereof showing the one-way valve incorporated therein;

FIGS. 5C & 5D are enlarged respective frontal and rear perspective views thereof showing one of the receptacles;

FIG. 6A is a perspective view of the second embodiment of the gangable injection port holder of the invention comprising snap-together segments; FIG. 6C is a right side elevational view thereof; FIG. 6D is a top elevational view thereof and FIG. 6E is a bottom elevational view thereof;

FIG. 7A is a perspective view of the third embodiment of the gangable injection port holder of the invention comprising snap-together segments and FIG. 7B is a top elevational view thereof.

Similar reference characters refer to similar parts throughout the several views of the drawings.

DETAILED DESCRIPTION OF THE PREFERRED EMBODIMENTS

Figure 1A:
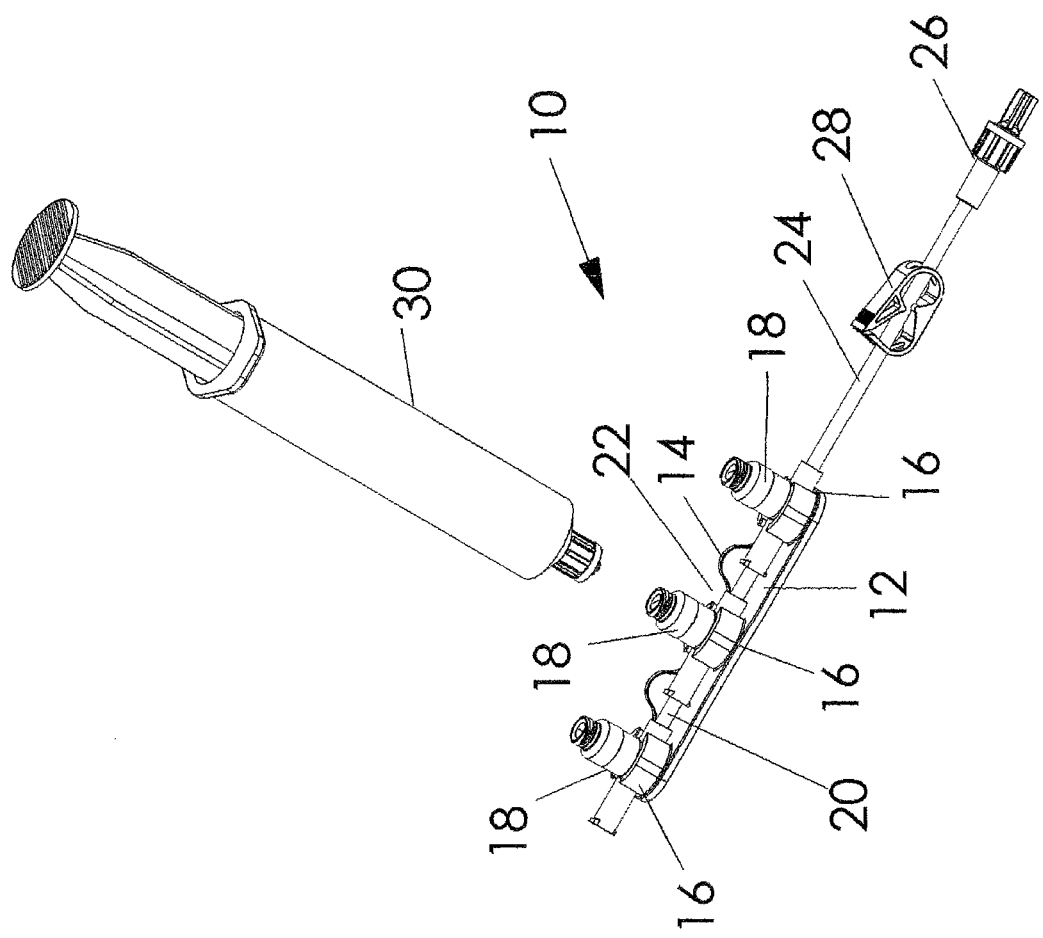
FIG. 1A is a perspective view of the first embodiment of the gangable injection port holder of the invention showing a conventional syringe oriented for connection to one of the valves.

As shown in FIGS. 1-5, the gangable port holder 10 of the invention comprises an elongated base 12 and an elongated side 14 positioned approximately 90 degrees relative to one another. A plurality of receptacles 16 are integrally formed with the elongated base 12. Corresponding swabable valves 18 interconnected in series by tubing 20 are positioned within the receptacles 16. The elongated side 14 comprises a plurality of castellations 22 in alignment with the receptacles 16.

The gangable port holder 10 may be connected in-line with the IV line from the IV bag to the patient with the first-most swabable valve 18 of the series is connected to a connection line 24 having a Luer connector 26 allowing the assembly to be connected to the IV line to the patient and with the last-most swabable valve 18 being connected to the IV line to the IV bag. A leaf valve 28 may be provided on the connection line 24 to close off the operation of the swabable valves from the IV line.

Figure 1B:
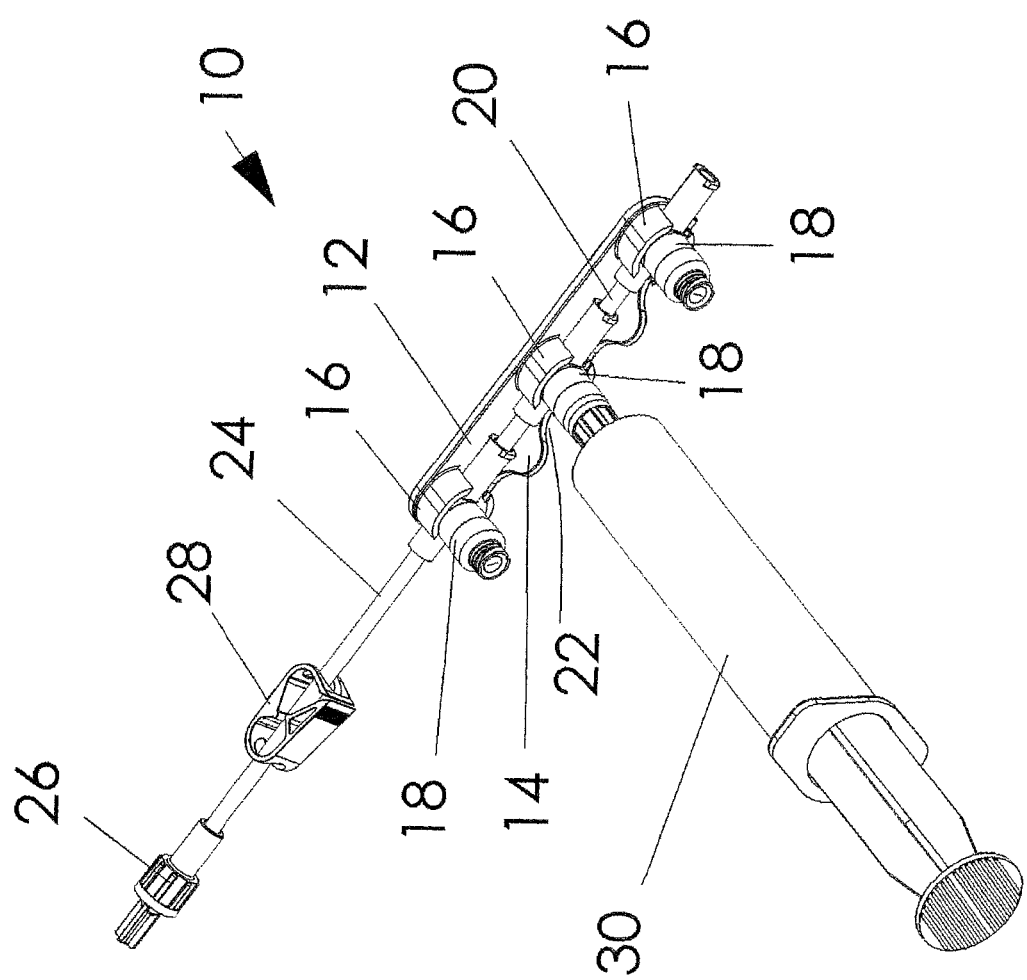

The gangable port holder 10 of the invention allows a plurality of syringes 30 (or other medical devices) containing medicine to be connected to the plurality of swabable valves and conveniently left in place throughout a surgical procedure, thereby allowing the selective administration of drugs to the patient via the IV line throughout the surgical procedure. As shown in FIG. 1B, the holder 10 with the syringes 30 connected may be laid on the side wall 14 on a table. Alternatively, as shown in FIG. 1C, the holder 10 may be used vertically by resting on the base wall 12.

Figure 2:
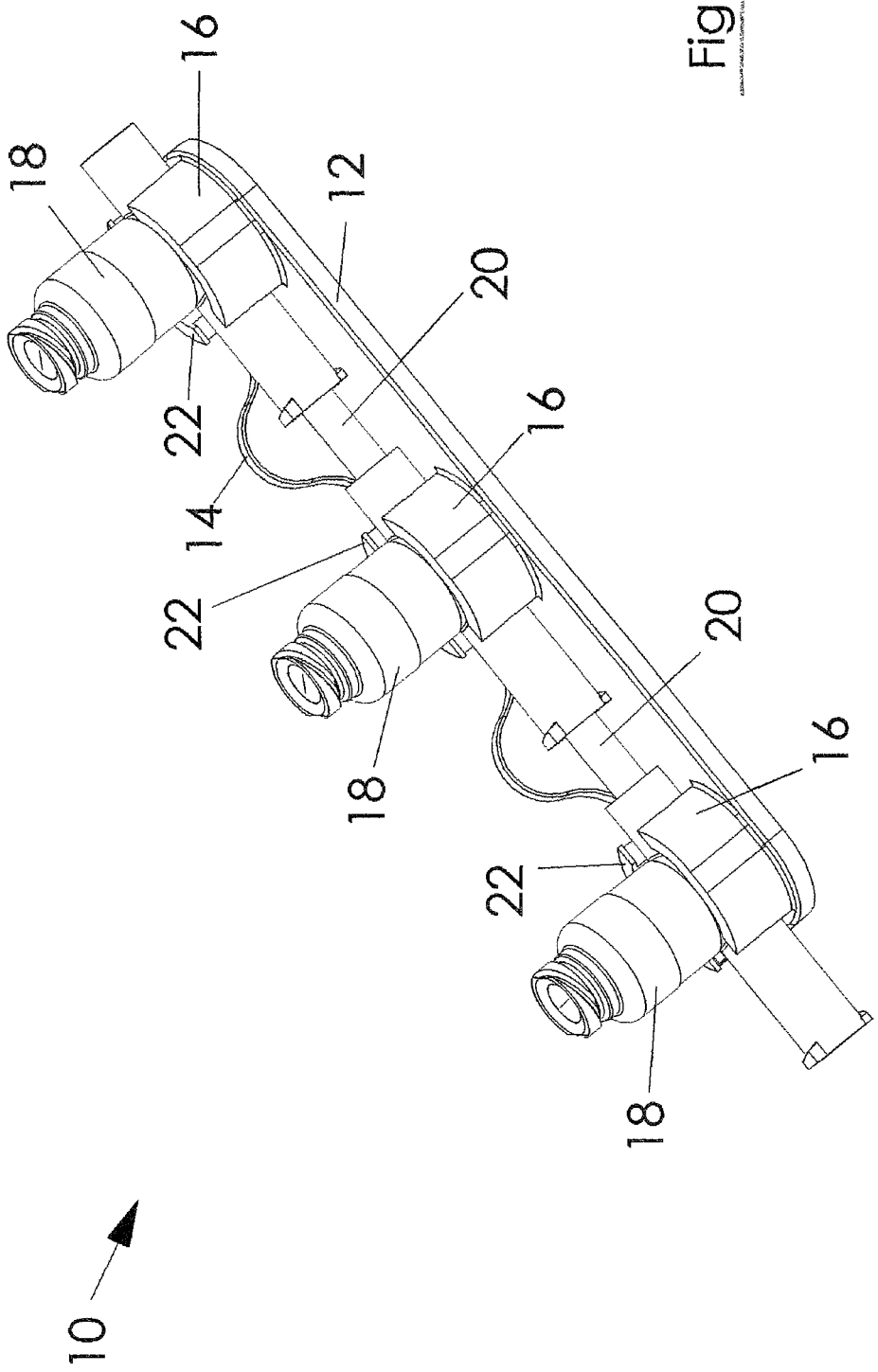
FIG. 2 is an enlarged perspective view of the holder and T-sites.
Figure 3:
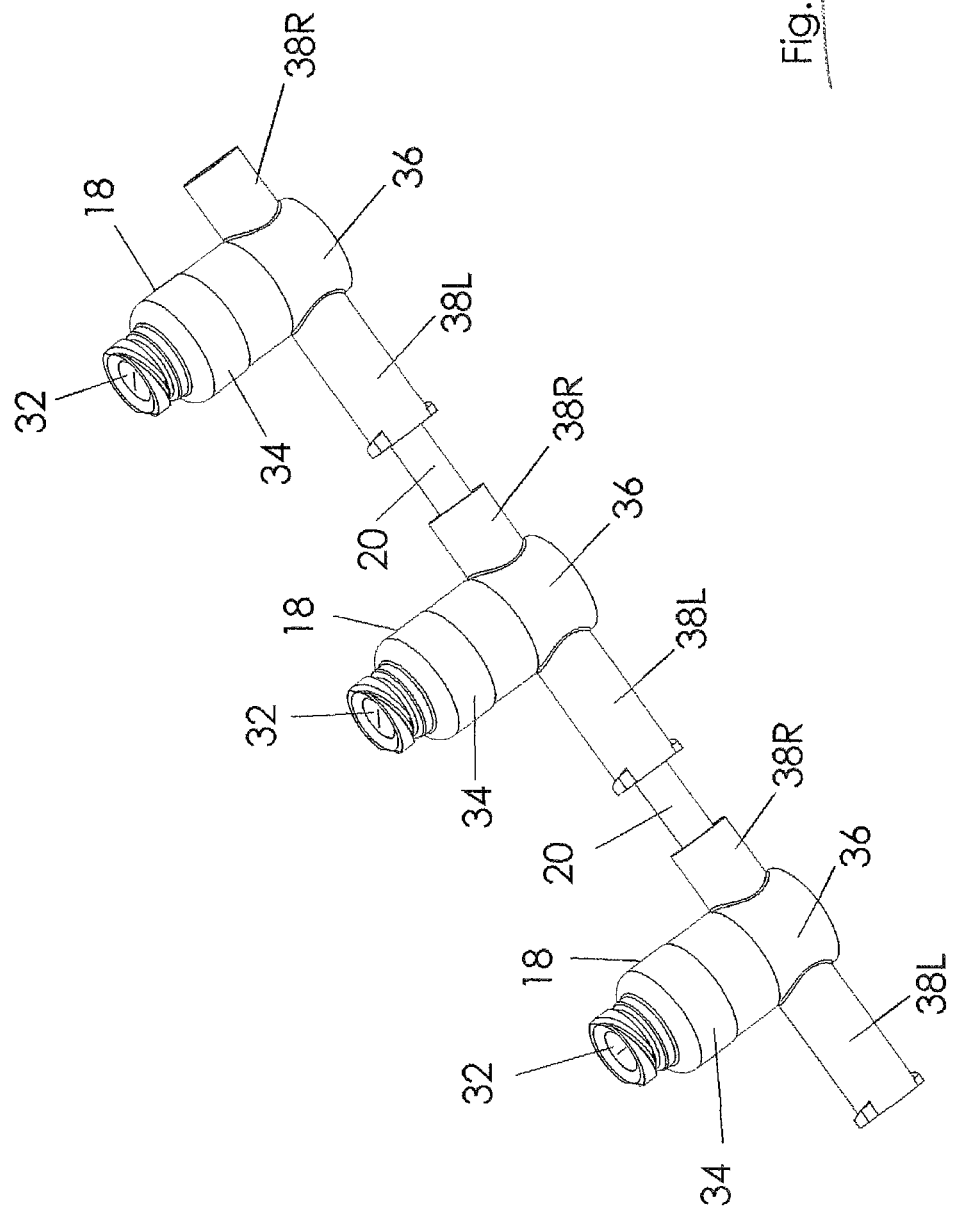
FIG. 3 is a perspective view of the swabable access valves after being removed from the holder.
Figure 5A:
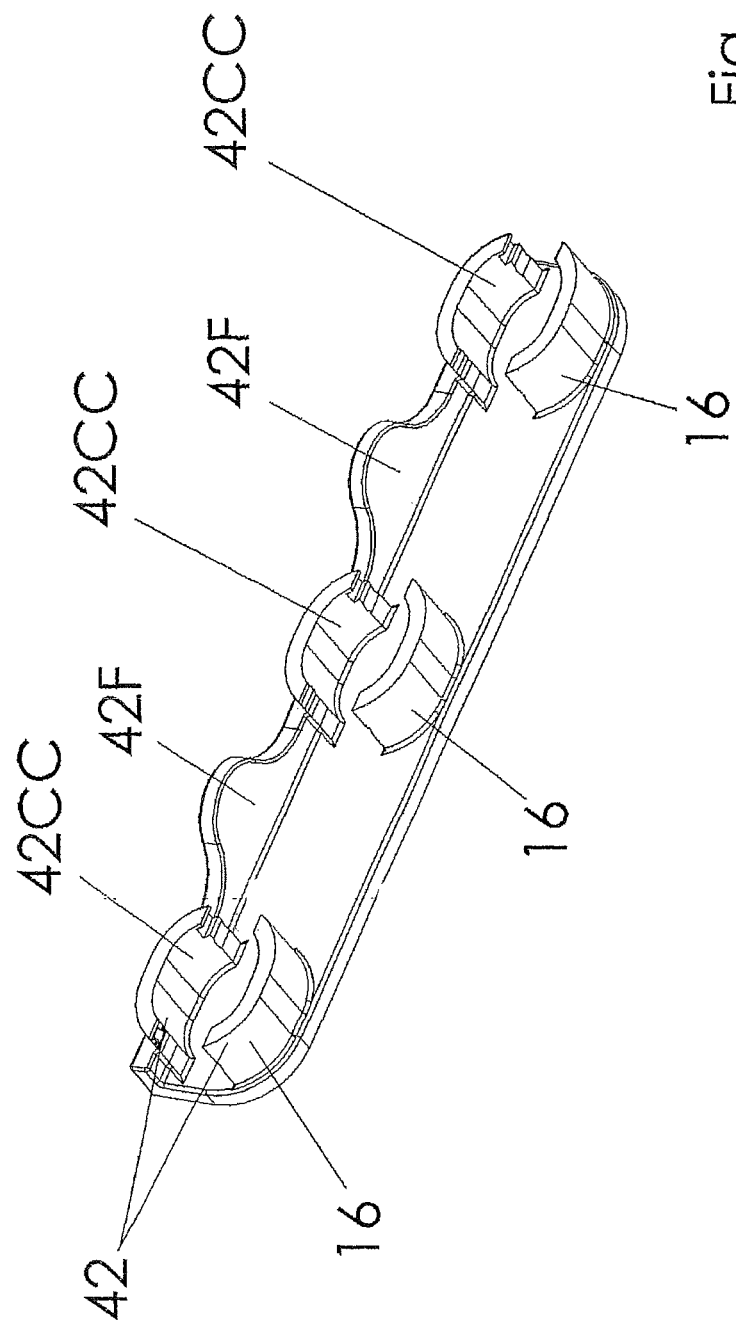
FIG. 5A is a perspective view of the first embodiment of the holder with the swabable access valves being removed therefrom.
Figure 5B:
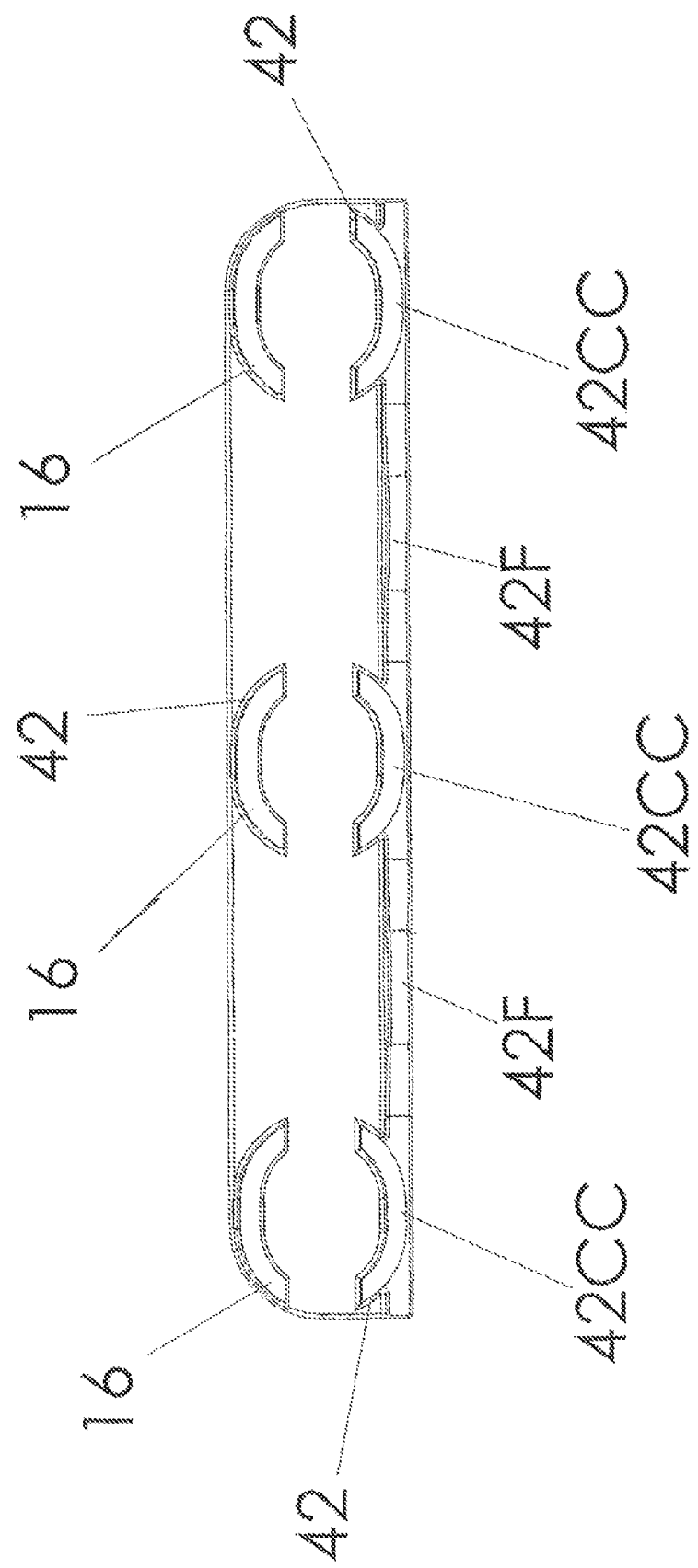
FIG. 5B is a top elevational view thereof.
Figure 6B:
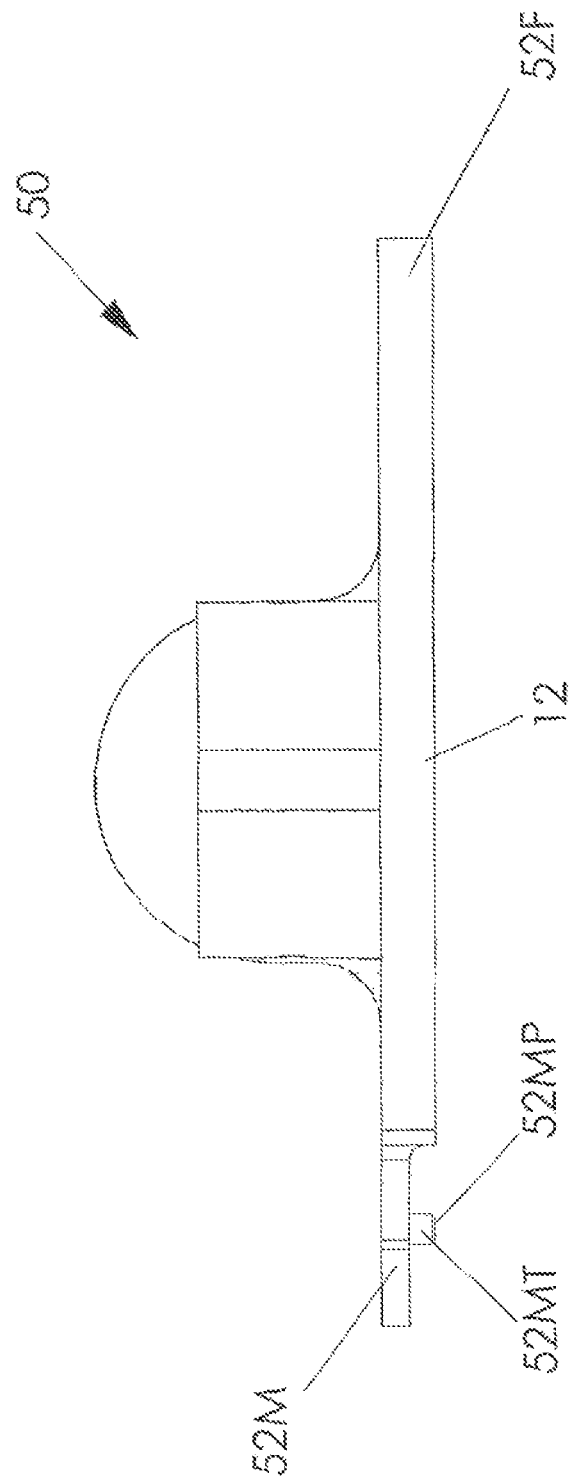
FIG. 6B is a front elevational view thereof.
Figure 6E:
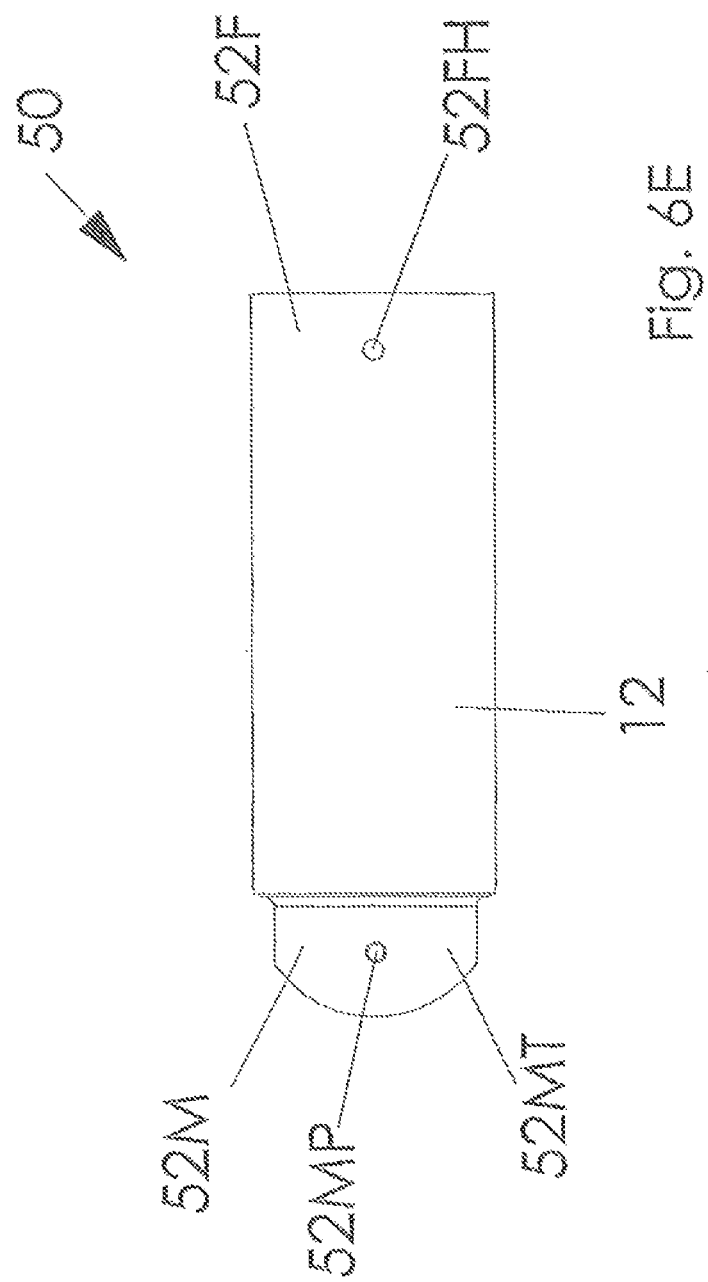

As shown in FIG. 2 compared with FIG. 3, the serially-connected swabable valves are assembled and then inserted as an assembly into the holder 10.

Referring now to FIGS. 4A-4C, each of the swabable valves 18 comprises a swabable valve element 32 mounted within a valve body 34. The valve element 32 and body 34 preferably comprises the type of valve element and body shown and described in U.S. Pat. No. 6,651,956, the disclosure of which is hereby incorporated by reference herein. The valve body 34 is connected to a housing 36 having tubular left and right side ports 38L and 38R extending from diametrically-opposing sides thereof, with tubing 20 interconnecting one valve's left side port 38L with its adjacent valve's right side port 38R such that they are serially connected.

A one-way check valve 40 is operatively positioned between the valve body 34 and the housing 36 to allow uni-directional fluid flow through the valve element 32 to flow into the side ports 38 (the reverse flow being checked by the one-way valve 40). While many types of one-way valves may suffice, preferably the one-way valve 40 comprises a generally circular diaphragm 40D with an enlarged annular edge 40E. The annular edge 40E is sealingly retained within annual groove 40G formed between the connection of the valve body 34 and the housing 36 with diaphragm 40D being urged into sealing engagement with the peripheral annular edge of the outlet 34O of the body 34. A plurality of apertures 40A are formed in the diaphragm 40D outside of outlet 34O allowing fluid to flow therethrough when the diaphragm 40D is unseated from the edge of the outlet 34O.

As noted above, the receptacles 16 function as sockets to receive the swabable valve 18. More particularly, as shown in FIGS. 5A-5D, each receptacle 16 comprises two arcuate side walls 42 that define the socket for receiving the swabable valve 18. The separation between the arcuate side walls 42 allows the side ports 38 to extend therebetween when the swabable valves 18 are installed in their respective receptacles 16.

The radius of the arcuate side walls 42 preferably corresponds to the radius of the housing 36 of the swabable valve 18. The side walls 42 may comprise one-half of a circular cylindrical configuration 42CC. Preferably, however, side walls 42 comprise an oval configuration including the circular cylindrical configuration 42CC separated by a flat portion 42F. In either configuration, the housing 36 of the swabable valve 18 is intended to snap-fit into the receptacle 16 using frictional snap grooves 42G.

It is noted that the series of swabable valves is intended to be assembled together by the interconnecting tubing 20 in the same spacing as the spacing between the respective receptacles 16. In this regard, the use of the oval configuration composed of the two circular cylindrical side walls 42CC and the flat wall 42F is preferred to allow some manufacturing variance should the swabable valves 18 not be precisely separated equidistantly to correspond to the spacing of the respective receptacles 16.

The second embodiment of the invention, as illustrated in FIG. 6A-6E, include receptacles 16 similarly configured as described above in connection with the first embodiment. However, in the second embodiment, the elongated base 12 and its integral elongated side 14 are segmented such that each segment 50 contains one receptacle 18, with each segment 50 interlocking with adjacent segments.

More particularly, the interlocking segments 50 each include at one end a male connector 52M and at the other end a female connector 52F that are complementarily configured to snap together. The configuration of the female connector 52F in the second embodiment includes a blind slot 52FB in the upper surface of the end of the base 12 that is configured and dimensioned to receive a complementary male tab 52MT to snap-fit together. For added tightness, the blind slot 52FB of the female connector 52F may comprise a detent hole 52FH and the male tab 52MT may comprise a complementarily configured detent protrusion 52MP that snap-fits into the female's detent hole 52MT.

Figure 7B:
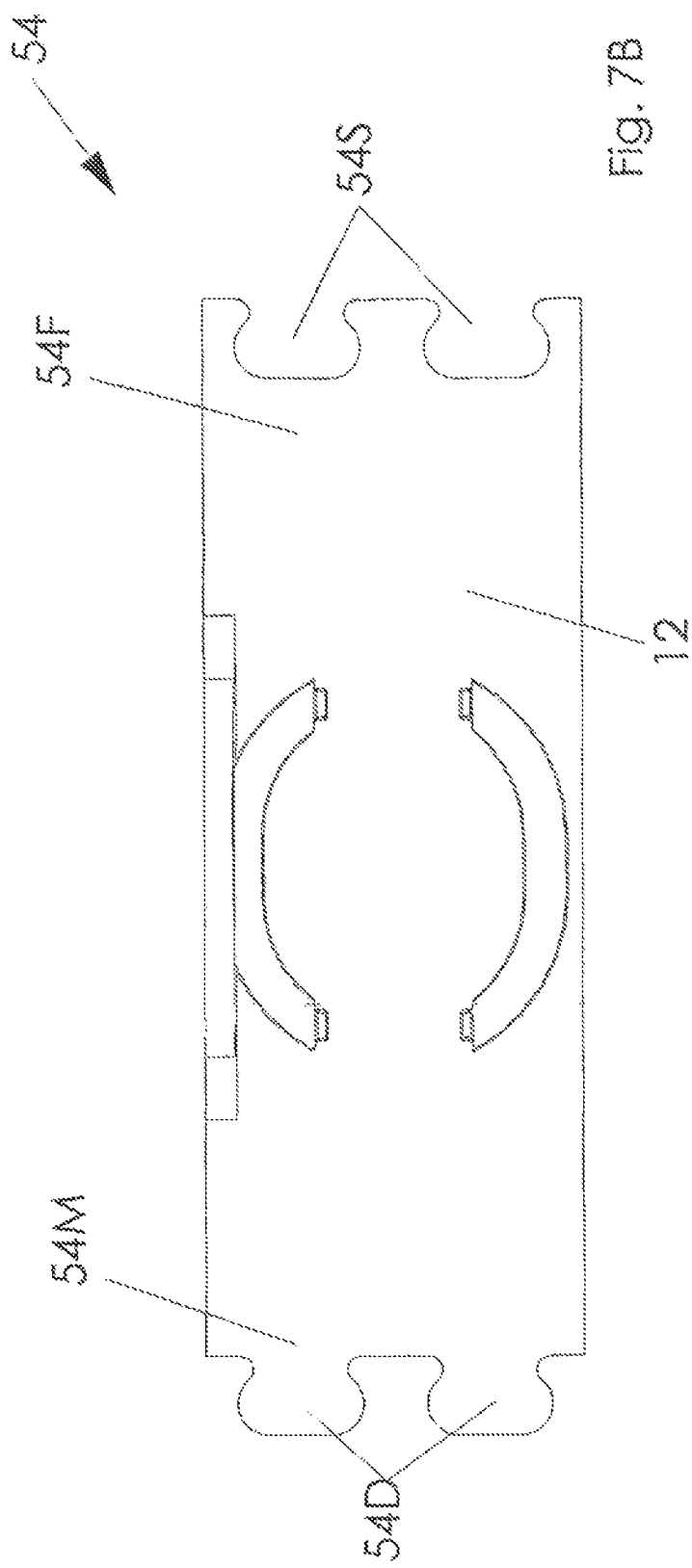

The third embodiment of the invention, as illustrated in FIG. 7A-7B, includes a base 12 composed of snap-together segments 54 as described above, but wherein the male connector 54M at one end and the female connector 54F at the other end are complementarily configured to snap together by virtue of a dovetail configuration. More specifically, the male connector 54M comprises a plurality of dovetails 54D that snap into a corresponding plurality of dovetail slots 54S of the female connector 54M.

Figure 8A:
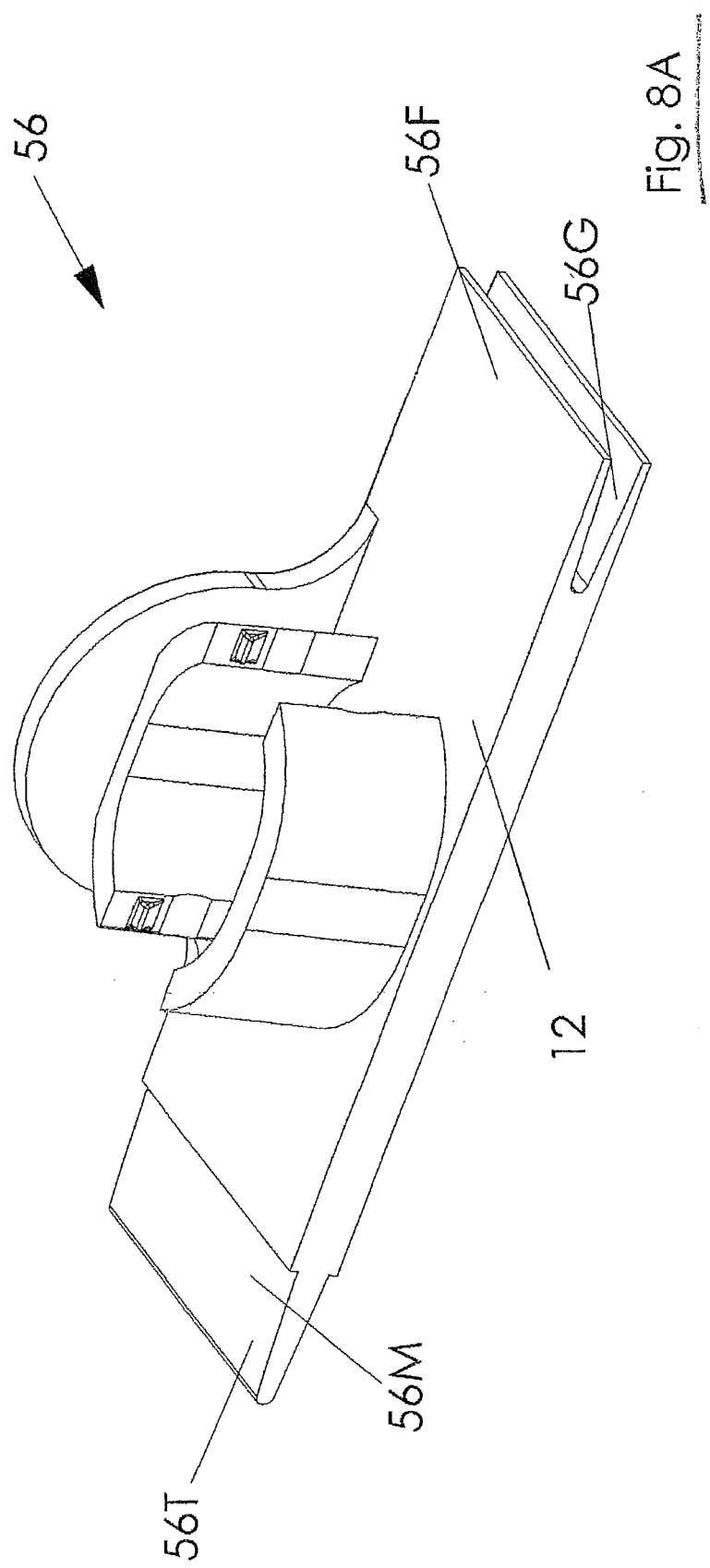
FIG. 8A is a perspective view of the forth embodiment of the gangable injection port holder of the invention comprising snap-together segments and FIG. 8B is a right side elevational view thereof.
Figure 8B:
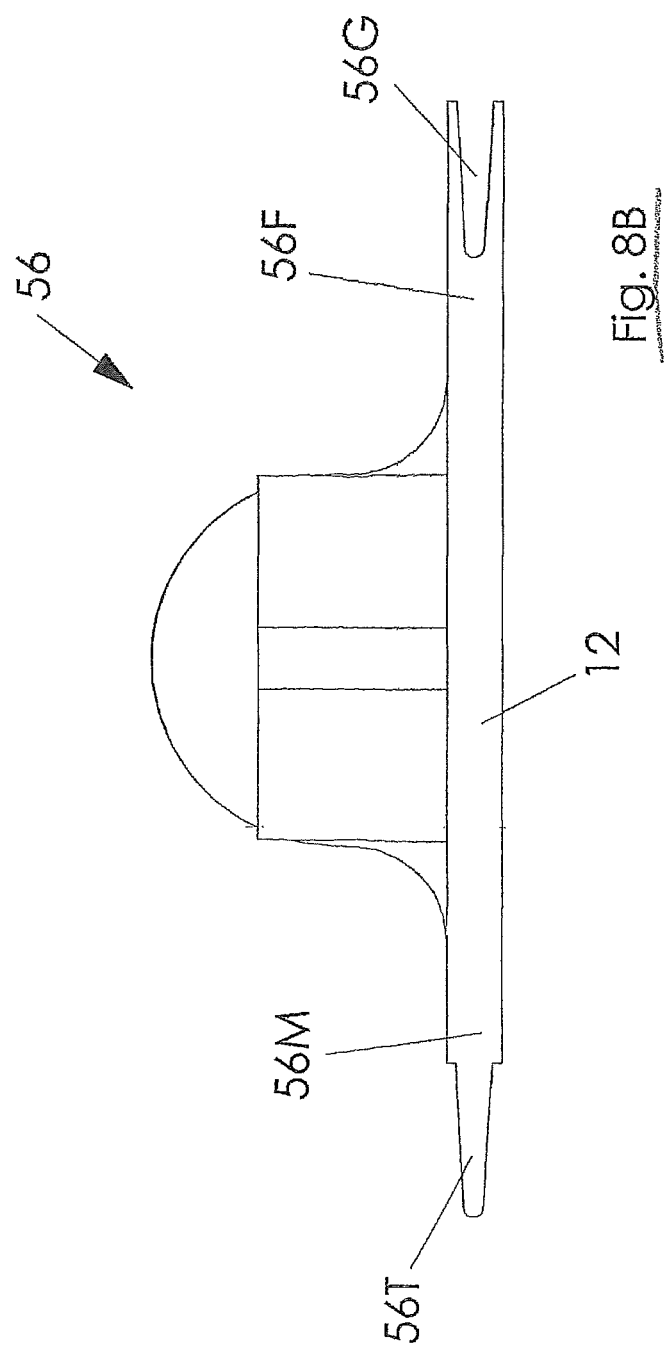

Finally, the forth embodiment, as illustrated in FIG. 8A-8B, includes a base 12 composed of snap-together segments 56 as described above, but the male connector 56M at one end and the female connector 56F at the other end are complementarily configured to snap together by virtue of a tongue and groove configuration. More specifically, the male connector 56M comprises a tongue 56T extending outwardly from the edge of the base 12 that snaps into a corresponding a groove 56G positioned along the edge of the base 12.

Many other configurations for snapping together the segmented base 12 may suffice without departing from the spirit and scope of this invention.

It can be appreciated that the interlocking segments 50, 54 and 56 allow any number of segments to be ganged together to correspond to the number of desired serially valves 18 to be utilized during a surgical procedure, thereby significantly reducing the inventory of the different combinations thereof.

The present disclosure includes that contained in the appended claims, as well as that of the foregoing description. Although this invention has been described in its preferred form with a certain degree of particularity, it is understood that the present disclosure of the preferred form has been made only by way of example and that numerous changes in the details of construction and the combination and arrangement of parts may be resorted to without departing from the spirit and scope of the invention.

Now that the invention has been described,

What is claimed is:

1. A gangable port holder, comprising in combination:
   an elongated base comprising a plurality of receptacles; and
   a plurality of swabable valves serially interconnected by tubing;
   said swabable valves being positioned within respective said receptacles;
   each said swabable valves having a housing dimensioned and configured to snap-fit into respective said receptacles;
   said serially-connected swabable valves being assembled and then inserted as an assembly into the holder;
   said swabable valves comprising a swabable valve element mounted within a valve body, said valve body being connected to said housing, said housing having tubular left and right side ports extending from diametrically-opposing sides thereof, with said tubing interconnecting one valve's left side port with its adjacent valve's right side port such that they are serially connected; and
   each said receptacles comprising two arcuate side walls defining a socket for receiving said swabable valve, a separation between said arcuate side walls allowing said side ports to extend therebetween when said swabable valves are installed in their respective said receptacles.

2. The gangable port holder as set forth in claim 1, further including an elongated side connected approximately perpendicular said elongated base.

3. The gangable port holder as set forth in claim 1, wherein an elongated side is integrally formed with said elongated base.

4. The gangable port holder as set forth in claim 1, wherein said elongated base comprises a plurality of castellations in alignment with said receptacles.

5. The gangable port holder as set forth in claim 1, wherein said port holder is connected in-line with an IV line from an IV bag to the patient.

6. The gangable port holder as set forth in claim 1, further including a plurality of syringes containing medicine to be connected to respective said plurality of swabable valves.

7. The gangable port holder as set forth in claim 1, wherein a radius of said arcuate side walls corresponds to a radius of said housing of said swabable valve.

8. The gangable port holder as set forth in claim 1, wherein said side walls comprise an oval configuration including a circular cylindrical configuration separated by a flat portion and dimensioned to allow said swabable valve to be snap-fitted into said receptacle.

9. The gangable port holder as set forth in claim 8, wherein said series of said swabable valves are assembled together by said interconnecting tubing in the same spacing as the spacing between the respective receptacles, with said oval configuration composed of said two circular cylindrical side walls and said flat wall allowing some manufacturing variance should said swabable valves not be precisely separated equidistantly to correspond to the spacing of said respective receptacles.

10. The gangable port holder as set forth in claim 1, further including a one-way check valve operatively positioned between said valve body and said housing to allow unidirectional fluid flow through said valve element to flow into the side ports and the reverse flow being checked by said one-way valve.

11. The gangable port holder as set forth in claim 10, wherein said one-way valve comprises a generally circular diaphragm with an enlarged annular edge sealingly retained within annual groove formed between a connection of said valve body and said housing with said diaphragm being urged into sealing engagement with said peripheral annular edge of an outlet of the body.

12. The gangable port holder as set forth in claim 11, wherein a plurality of apertures are formed in said diaphragm outside of said outlet allowing fluid to flow therethrough when said diaphragm is unseated from said outlet.

13. The gangable port holder as set forth in claim 1, wherein said elongated base is segmented such that each said segment contains at least one said receptacle, with each said segment serially interlocking with adjacent said segments.

14. The gangable port holder as set forth in claim 13, wherein said interlocking said segments each include at one end a male connector and at another end a female connector that are complementarily configured to snap together.

15. The gangable port holder as set forth in claim 14, wherein a configuration of said female connector comprises a blind slot in at least an upper surface of said one end of said segment and a complementary male tab in said another, said blind slot and male tab being configured and dimensioned to snap-fit together.

16. The gangable port holder as set forth in claim 15, wherein said blind slot of said female connector comprises a detent hole and wherein said male tab comprises a complementarily configured detent protrusion that snap-fits into said detent hole of said female connector.

17. The gangable port holder as set forth in claim 14, wherein said male connector at said one end and said female connector at said another end are complementarily configured to snap together by virtue of a dovetail configuration.

18. The gangable port holder as set forth in claim 17, wherein said male connector comprises a plurality of dovetails that snap into a corresponding plurality of said dovetail slots of said female connector.

19. The gangable port holder as set forth in claim 14, wherein said male connector at said one end and the female connector at said another end are complementarily configured to snap together by virtue of a tongue and groove configuration.

20. The gangable port holder as set forth in claim 19, wherein said male connector comprises an outwardly extending tongue that snaps into a corresponding groove in said female connector.

* * * * *